(12) United States Patent
Goldfarb et al.

(10) Patent No.: US 8,748,568 B2
(45) Date of Patent: Jun. 10, 2014

(54) ISOLATED A-TYPE FHF N-TERMINAL DOMAIN PEPTIDES AND METHODS OF USE

(75) Inventors: Mitchell Goldfarb, River Edge, NJ (US); Dover Katarzyna, Riverdale, NY (US)

(73) Assignee: Research Foundation of The City University of New York, New York, NY (US)

( * ) Notice: Subject to any disclaimer, the term of this patent is extended or adjusted under 35 U.S.C. 154(b) by 7 days.

(21) Appl. No.: 13/319,016

(22) PCT Filed: May 6, 2010

(86) PCT No.: PCT/US2010/033885
§ 371 (c)(1),
(2), (4) Date: Jun. 12, 2012

(87) PCT Pub. No.: WO2010/129784
PCT Pub. Date: Nov. 11, 2010

(65) Prior Publication Data
US 2012/0244615 A1    Sep. 27, 2012

Related U.S. Application Data

(60) Provisional application No. 61/175,951, filed on May 6, 2009.

(51) Int. Cl.
*C07K 14/47* (2006.01)
*C12N 15/861* (2006.01)
*A61K 38/00* (2006.01)
*C07K 2/00* (2006.01)

(52) U.S. Cl.
CPC ............... *C07K 14/47* (2013.01); *C12N 15/861* (2013.01)
USPC ........................................................ 530/300

(58) Field of Classification Search
CPC ............ C07K 14/47; C07K 2/00; C07K 4/00; C07K 5/00; C07K 7/00; C07K 14/00; C07K 16/00; C07K 17/00; C12N 15/861; A61K 38/00
USPC ........................................................ 530/300
See application file for complete search history.

(56) References Cited

U.S. PATENT DOCUMENTS 5,876,967 A * 3/1999 Nathans et al. ............... 435/69.4

OTHER PUBLICATIONS

Rush, A.M. et al., Differential modulation of sodium channel Nav1.6 by two members of the fibroblast growth factor homologous factor 2 subfamily, Eur. J. Neurosci., 2006, vol. 23, pp. 2551-2562.
Goetz, R. et a., Crystal structure of a fibroblast growth factor homologous factor (FHF) defines a conserved surface on FHF's for binding and modulation of voltage-gated sodium channels, The Journal of Biological Chemistry, Apr. 30 2009, vol. 284, No. 26, pp. 17883-17896.
Goldfarb, M. et al., Fibroblast growth factor homologous factors control neuronal excitability through modulation of voltage-gated sodium channels, Neuron, 2007, vol. 55, pp. 449-463.
Laezza, F., et al., FGF14 N-terminal splice variants differentially modulate Nav1.2 and Nav1.6-encoded sodium channels, Mol. Cell Neurosci., May 22, 2009, vol. 42, pp. 90-101.

* cited by examiner

*Primary Examiner* — Christina Bradley
*Assistant Examiner* — Kristina M Hellman
(74) *Attorney, Agent, or Firm* — Hoffmann & Baron, LLP

(57) ABSTRACT

Isolated peptides are provided that are effective in inducing long-term inactivation of voltage-gated sodium channels (VGSCs) in mammalian cells. Such peptides are useful in reducing the action potentials of these excitable cells, for example, neurons, myocytes, and tonic muscle cells, in mammals in need thereof.

13 Claims, 9 Drawing Sheets

FIGURE 1A

FHF Alignment

```
hFHF-1B  protein  1  MESKEPQLK                                                                                    9
hFHF-2B  protein  1  MALLRKSY-SEPQLK                                                                             14
hFHF4b   protein  1  MVKPVPLFRRTDFKLLCNHKDLFFLRVSKLL                                                              
mFHF-1A  protein  1  MAAAIASSLIRQKRQARESNSDRVSASK                                                                 
hFHF-2A  protein  1  MAAAIASSLIRQKRQARER--EKSNACK                                                                 
hFHF-4A  protein  1  MAAAIASGLIRQKRQAREQHWDRPSASR                                                                 
hFHF-3A  protein  1  MAALASSLIRQKREVREPGGSRPVSAQ                                                                  
```

```
                  MALLRKSLKKNKPTDPQLK                                    74
         DCFSPKSM-WFLWNIFSKGTHMLQCLCGKSLKKNPTDPQLK                        77
         RRSSPSKDGRSLCDRHVLGVFSKVRFCSGRKRPVRRPEPQLK                        67
         CVSSPSKG-KTSCDKNKLNVFSRVKLFGSKKRRRR--PEPQLK                       69
         RRSSPSKN-RGLCNGNLVDIESKVRIFGLKKRRLRR-QDPQLK                       69
         RRVCPRGT-KSLCQKQLILLSKVRLCGGRPARPDRGPEPQLK                        
```

FIGURE 1B

| | | | | | |
|---|---|---|---|---|---|
| 10 | GIVTRL | FSQQGYF | LQMHPDGT | IDGTKDENSDY | | |
| 15 | GIVTKL | YSRQGYH | LQLQADGT | HDGTKDEDSTY | | |
| 75 | GIVTRL | YCRQGYL | LQMHPDGA | LDGTKDDSTNS | | |
| 72 | GIVTRL | FSQQGYF | LQMHPDGT | IDGTKDENSDY | | |
| 68 | GIVTKL | YSRQGYH | LQLQADGT | IDGTKDEDSTY | | |
| 70 | GIVTRL | YCRQGYL | LQMHPDGA | LDGTKDDSTNS | | |
| 70 | GIVTKL | FCRQGFY | LQANPDGS | IQGTPEDTSSF | | |

| | | | | | |
|---|---|---|---|---|---|
| 85 | TLFNLIPVGLRVV | AIQGVKIA | SLYVAMNGEGYLY | SSDVFTPECK | 84 |
| 90 | TLFNLIPVGLRVV | AIQGVKIA | SLYLAMNSEGYLY | SSELFTPECK | 89 |
| 150 | TLFNLIPVGLRVV | AIQGVKT | GLYIAMNGEGYLY | SSDVFTPECK | 149 |
| 147 | TLFNLIPVGLRVV | AIQGVKIA | SLYVAMNGEGYLY | SSELFTPECK | 146 |
| 143 | TLFNLIPVGLRVV | AIQGVKT | GLYIAMNSEGYLY | SSELFTPECK | 142 |
| 145 | TLFNLIPVGLRVV | AIQGVKT | GLYLAMNAEGLLYS | SPHFTPECK | 144 |
| 145 | THFNLIPVGLRVV | TIQSAKL | GHYMAMNAEGLLY | SSPHFTAECR | 144 |

| | | | | | |
|---|---|---|---|---|---|
| 85 | FKESVFENYY | VIYSST | LYRQQESGRAW | FLGLNKEGQI |
| 90 | FKESVFENYY | VIYSSMI | YRQQSGRAW | YLGLNKEGEI |
| 150 | FKESVFENYY | VIYSSML | YRQQESGRAW | FLGLNKEGQA |
| 147 | FKESVFENYY | VIYSSTL | YRQQESGRAW | FLGLNKEGPI |
| 143 | FKESVFENYY | VIYSSMI | YRQQSGRAW | YLGLNKEGEI |
| 145 | FKESVFENYY | VIYSSML | YRQQESGRAW | FLGLNKEGQA |
| 145 | FKECVFENYY | VLYASAL | YRQRRSGRAW | YLGLDKEGQV |

FIGURE 1C

```
MKGNRVKKTKPSSHFVPKPIEVCMYREPSLHEIGEKQG  159
MKGNHVKKNKPAAHFLPKPLKVAMYKEPSLHDLTEFSR  164
MKGNRVKKTKPAAHFLPKPLEVAMYREPSLHDVGETVP  224
MKGNRVKKTKPSSHFVPKPIEVCMYREPSLHEIGEKQG  221
MKGNHVKKNKPAAHFLPKPLKVAMYKEPSLHDLTEFSR  217
MKGNRVKKTKPAAHFLPKPLEVAMYREPSLHDVGETVP  219
MKGNRVKKTKAAAHFLPKLLEVAMYQEPSLHSVPEASP  219
```
(SEQ ID NO: 5)
(SEQ ID NO: 6)
(SEQ ID NO: 7)
(SEQ ID NO: 8)
(SEQ ID NO: 9)
(SEQ ID NO: 10)
(SEQ ID NO: 11)

```
160 R----SRKSSGTPTMNGGKVNQDST*      182
165 SGSGTPTKSRSVSGVLNGGKSMSHNEST    192
225 KPGVTPSKSTSAIMNGGKPVNKSKTT*    253
222 R----SRKSSGTPTMNGGKVNQDST       243
218 SGSGTPTKSRSVSGVLNGGKSMSHNEST    245
220 KPGVTPSKSTSAIMNGGKPVNKSKTT      247
220 S----SPPAP                      225
```

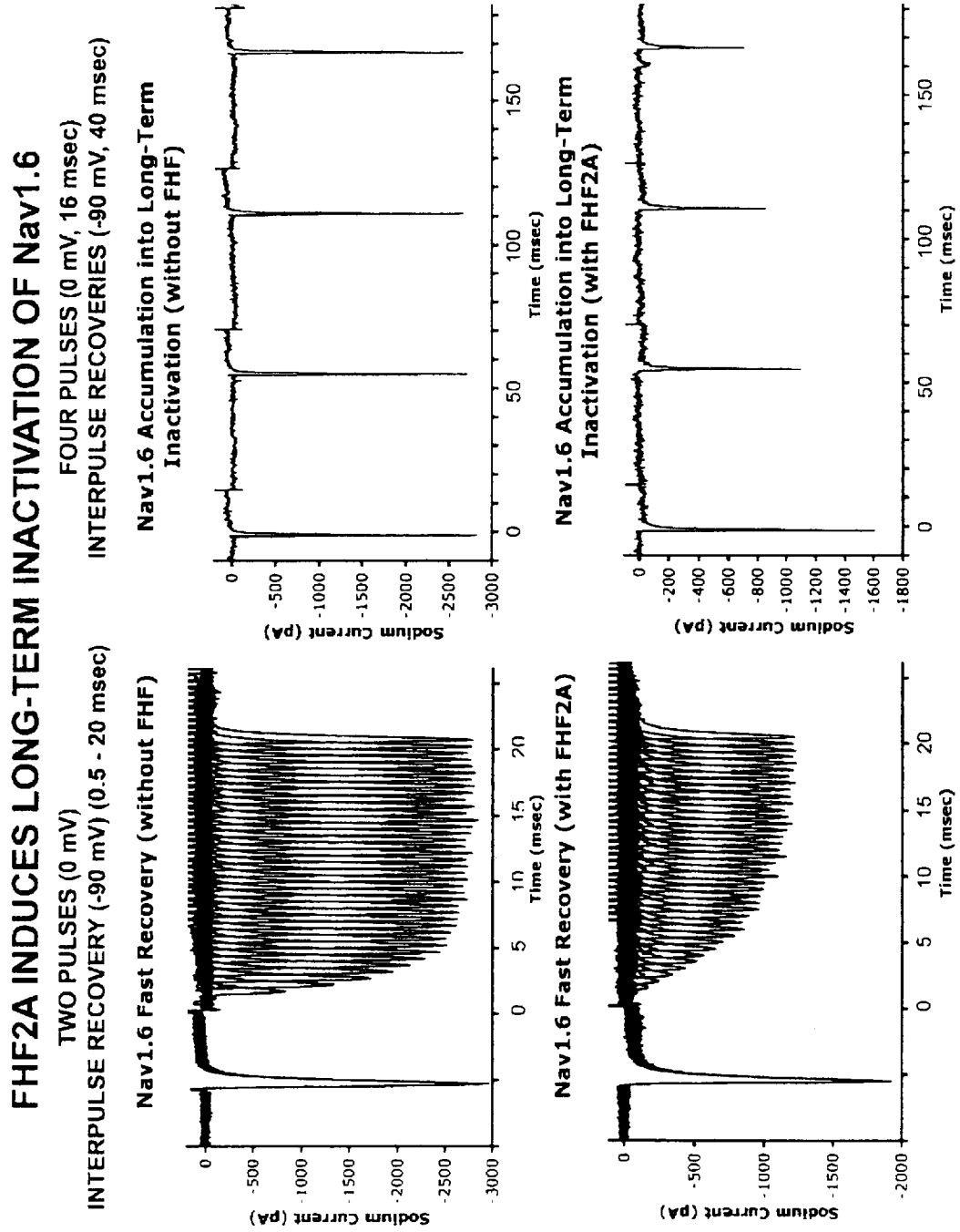

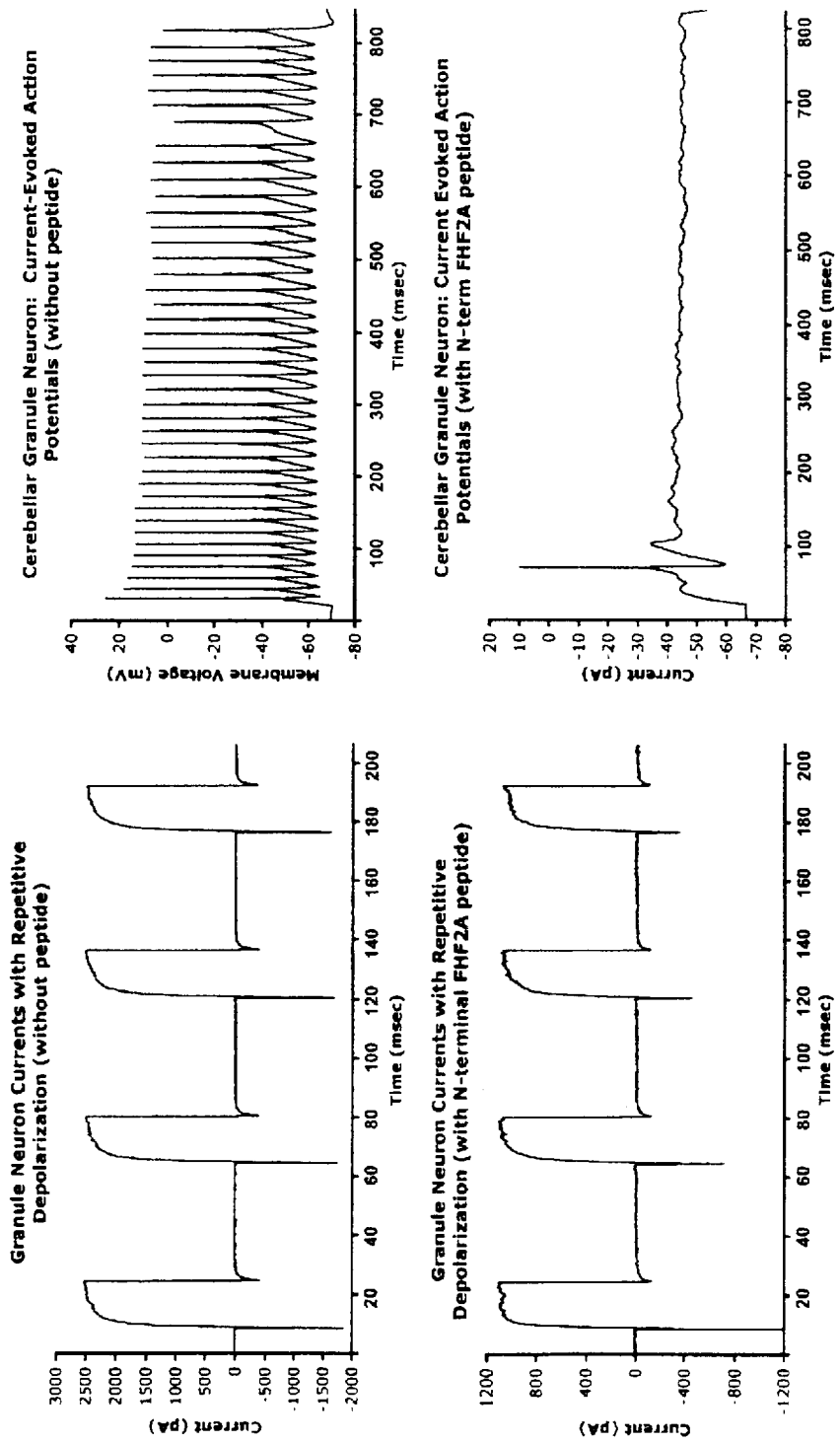

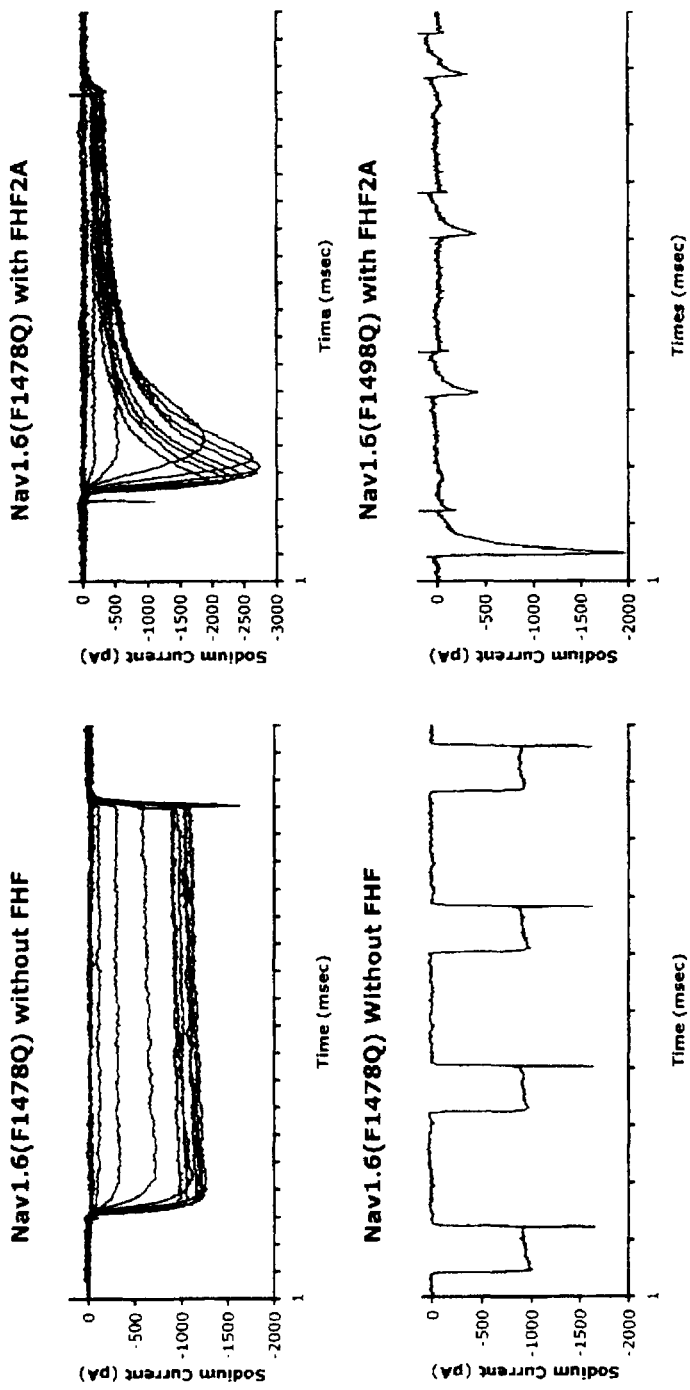

SEQUENCE LISTING

```
<160> NUMBER OF SEQ ID NOS: 12

<210> SEQ ID NO 1
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 1

Ala Ala Ala Ile Ala Ser Ser Leu Ile Arg Gln Lys Arg Gln Ala Arg
1               5                   10                  15

Glu Ser Asn Ser
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 2

Ala Ala Ala Ile Ala Ser Ser Leu Ile Arg Gln Lys Arg Gln Ala Arg
1               5                   10                  15

Glu Arg Glu Lys
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 3

Ala Ala Leu Ala Ser Ser Leu Ile Arg Gln Lys Arg Glu Val Arg Glu
1               5                   10                  15

Pro Gly Gly Ser
            20
```

-continued

```
<210> SEQ ID NO 4
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 4

Ala Ala Ala Ile Ala Ser Gly Leu Ile Arg Gln Lys Arg Gln Ala Arg
1               5                   10                  15

Glu Gln His Trp
            20

<210> SEQ ID NO 5
<211> LENGTH: 181
<212> TYPE: PRT
<213> ORGANISM: Artificial Sequence
<220> FEATURE:
<223> OTHER INFORMATION: Synthetic amino acid sequence: hFHF-1B

<400> SEQUENCE: 5

Met Glu Ser Lys Glu Pro Gln Leu Lys Gly Ile Val Thr Arg Leu Phe
1               5                   10                  15

Ser Gln Gln Gly Tyr Phe Leu Gln Met His Pro Asp Gly Thr Ile Asp
            20                  25                  30

Gly Thr Lys Asp Glu Asn Ser Asp Tyr Thr Leu Phe Asn Leu Ile Pro
        35                  40                  45

Val Gly Leu Arg Val Val Ala Ile Gln Gly Val Lys Ala Ser Leu Tyr
    50                  55                  60

Val Ala Met Asn Gly Glu Gly Tyr Leu Tyr Ser Ser Asp Val Phe Thr
65                  70                  75                  80

Pro Glu Cys Lys Phe Lys Glu Ser Val Phe Glu Asn Tyr Tyr Val Ile
                85                  90                  95

Tyr Ser Ser Thr Leu Tyr Arg Gln Gln Glu Ser Gly Arg Ala Trp Phe
            100                 105                 110

Leu Gly Leu Asn Lys Glu Gly Gln Ile Met Lys Gly Asn Arg Val Lys
        115                 120                 125

Lys Thr Lys Pro Ser Ser His Phe Val Pro Lys Pro Ile Glu Val Cys
    130                 135                 140

Met Tyr Arg Glu Pro Ser Leu His Glu Ile Gly Glu Lys Gln Gly Arg
145                 150                 155                 160

Ser Arg Lys Ser Ser Gly Thr Pro Thr Met Asn Gly Gly Lys Val Val
                165                 170                 175

Asn Gln Asp Ser Thr
            180

<210> SEQ ID NO 6
<211> LENGTH: 192
<212> TYPE: PRT
<213> ORGANISM: Artificial Sequence
<220> FEATURE:
<223> OTHER INFORMATION: Synthetic amino acid sequence: hFHF-2B

<400> SEQUENCE: 6

Met Ala Leu Leu Arg Lys Ser Tyr Ser Glu Pro Gln Leu Lys Gly Ile
1               5                   10                  15

Val Thr Lys Leu Tyr Ser Arg Gln Gly Tyr His Leu Gln Leu Gln Ala
            20                  25                  30

Asp Gly Thr Ile Asp Gly Thr Lys Asp Glu Asp Ser Thr Tyr Thr Leu
        35                  40                  45
```

```
Phe Asn Leu Ile Pro Val Gly Leu Arg Val Val Ala Ile Gln Gly Val
             50                  55                  60

Gln Thr Lys Leu Tyr Leu Ala Met Asn Ser Glu Gly Tyr Leu Tyr Thr
 65                  70                  75                  80

Ser Glu Leu Phe Thr Pro Glu Cys Lys Phe Lys Glu Ser Val Phe Glu
                 85                  90                  95

Asn Tyr Tyr Val Thr Tyr Ser Ser Met Ile Tyr Arg Gln Gln Gln Ser
                100                 105                 110

Gly Arg Gly Trp Tyr Leu Gly Leu Asn Lys Glu Gly Glu Ile Met Lys
            115                 120                 125

Gly Asn His Val Lys Lys Asn Lys Pro Ala Ala His Phe Leu Pro Lys
130                 135                 140

Pro Leu Lys Val Ala Met Tyr Lys Glu Pro Ser Leu His Asp Leu Thr
145                 150                 155                 160

Glu Phe Ser Arg Ser Gly Ser Gly Thr Pro Thr Lys Ser Arg Ser Val
                165                 170                 175

Ser Gly Val Leu Asn Gly Gly Lys Ser Met Ser His Asn Glu Ser Thr
                180                 185                 190

<210> SEQ ID NO 7
<211> LENGTH: 252
<212> TYPE: PRT
<213> ORGANISM: Artificial Sequence
<220> FEATURE:
<223> OTHER INFORMATION: Synthetic amino acid sequence: hFHF4b

<400> SEQUENCE: 7

Met Val Lys Pro Val Pro Leu Phe Arg Arg Thr Asp Phe Lys Leu Leu
 1               5                  10                  15

Leu Cys Asn His Lys Asp Leu Phe Phe Leu Arg Val Ser Lys Leu Leu
                 20                  25                  30

Asp Cys Phe Ser Pro Lys Ser Met Trp Phe Leu Trp Asn Ile Phe Ser
             35                  40                  45

Lys Gly Thr His Met Leu Gln Cys Leu Cys Gly Lys Ser Leu Lys Lys
 50                  55                  60

Asn Lys Asn Pro Thr Asp Pro Gln Leu Lys Gly Ile Val Thr Arg Leu
 65                  70                  75                  80

Tyr Cys Arg Gln Gly Tyr Tyr Leu Gln Met His Pro Asp Gly Ala Leu
                 85                  90                  95

Asp Gly Thr Lys Asp Asp Ser Thr Asn Ser Thr Leu Phe Asn Leu Ile
                100                 105                 110

Pro Val Gly Leu Arg Val Val Ala Ile Gln Gly Val Lys Thr Gly Leu
            115                 120                 125

Tyr Ile Ala Met Asn Gly Glu Gly Tyr Leu Tyr Pro Ser Glu Leu Phe
130                 135                 140

Thr Pro Glu Cys Lys Phe Lys Glu Ser Val Phe Glu Asn Tyr Tyr Val
145                 150                 155                 160

Ile Tyr Ser Ser Met Leu Tyr Arg Gln Gln Glu Ser Gly Arg Ala Trp
                165                 170                 175

Phe Leu Gly Leu Asn Lys Glu Gly Gln Ala Met Lys Gly Asn Arg Val
                180                 185                 190

Lys Lys Thr Lys Pro Ala Ala His Phe Leu Pro Lys Pro Leu Glu Val
            195                 200                 205

Ala Met Tyr Arg Glu Pro Ser Leu His Asp Val Gly Glu Thr Val Pro
210                 215                 220
```

-continued

```
Lys Pro Gly Val Thr Pro Ser Lys Ser Thr Ser Ala Ser Ala Ile Met
225                 230                 235                 240

Asn Gly Gly Lys Pro Val Asn Lys Ser Lys Thr Thr
                245                 250
```

<210> SEQ ID NO 8
<211> LENGTH: 243
<212> TYPE: PRT
<213> ORGANISM: Artificial Sequence
<220> FEATURE:
<223> OTHER INFORMATION: Synthetic amino acid sequence: mFHF-1A

<400> SEQUENCE: 8

```
Met Ala Ala Ile Ala Ser Ser Leu Ile Arg Gln Lys Arg Gln Ala
1               5                   10                  15

Arg Glu Ser Asn Ser Asp Arg Val Ser Ala Ser Lys Arg Arg Ser Ser
                20                  25                  30

Pro Ser Lys Asp Gly Arg Ser Leu Cys Asp Arg His Val Leu Gly Val
            35                  40                  45

Phe Ser Lys Val Arg Phe Cys Ser Gly Arg Lys Arg Pro Val Arg Arg
    50                  55                  60

Arg Pro Glu Pro Gln Leu Lys Gly Ile Val Thr Arg Leu Phe Ser Gln
65                  70                  75                  80

Gln Gly Tyr Phe Leu Gln Met His Pro Asp Gly Thr Ile Asp Gly Thr
                85                  90                  95

Lys Asp Glu Asn Ser Asp Tyr Thr Leu Phe Asn Leu Ile Pro Val Gly
            100                 105                 110

Leu Arg Val Val Ala Ile Gln Gly Val Lys Ala Ser Leu Tyr Val Ala
        115                 120                 125

Met Asn Gly Glu Gly Tyr Leu Tyr Ser Ser Asp Val Phe Thr Pro Glu
    130                 135                 140

Cys Lys Phe Lys Glu Ser Val Phe Glu Asn Tyr Tyr Val Ile Tyr Ser
145                 150                 155                 160

Ser Thr Leu Tyr Arg Gln Gln Glu Ser Gly Arg Ala Trp Phe Leu Gly
                165                 170                 175

Leu Asn Lys Glu Gly Gln Ile Met Lys Gly Asn Arg Val Lys Lys Thr
            180                 185                 190

Lys Pro Ser Ser His Phe Val Pro Lys Pro Ile Glu Val Cys Met Tyr
        195                 200                 205

Arg Glu Pro Ser Leu His Glu Ile Gly Glu Lys Gln Gly Arg Ser Arg
    210                 215                 220

Lys Ser Ser Gly Thr Pro Thr Met Asn Gly Gly Lys Val Val Asn Gln
225                 230                 235                 240

Asp Ser Thr
```

<210> SEQ ID NO 9
<211> LENGTH: 245
<212> TYPE: PRT
<213> ORGANISM: Artificial Sequence
<220> FEATURE:
<223> OTHER INFORMATION: Synthetic amino acid sequence: hFHF-2A

<400> SEQUENCE: 9

```
Met Ala Ala Ile Ala Ser Ser Leu Ile Arg Gln Lys Arg Gln Ala
1               5                   10                  15

Arg Glu Arg Glu Lys Ser Asn Ala Cys Lys Cys Val Ser Ser Pro Ser
                20                  25                  30

Lys Gly Lys Thr Ser Cys Asp Lys Asn Lys Leu Asn Val Phe Ser Arg
```

-continued

```
                   35                  40                  45
Val Lys Leu Phe Gly Ser Lys Arg Arg Arg Arg Pro Glu Pro
 50                  55                  60
Gln Leu Lys Gly Ile Val Thr Lys Leu Tyr Ser Arg Gln Gly Tyr His
 65                  70                  75                  80
Leu Gln Leu Gln Ala Asp Gly Thr Ile Asp Gly Thr Lys Asp Glu Asp
                     85                  90                  95
Ser Thr Tyr Thr Leu Phe Asn Leu Ile Pro Val Gly Leu Arg Val Val
                100                 105                 110
Ala Ile Gln Gly Val Gln Thr Lys Leu Tyr Leu Ala Met Asn Ser Glu
                115                 120                 125
Gly Tyr Leu Tyr Thr Ser Glu Leu Phe Thr Pro Glu Cys Lys Phe Lys
                130                 135                 140
Glu Ser Val Phe Glu Asn Tyr Tyr Val Thr Tyr Ser Ser Met Ile Tyr
145                 150                 155                 160
Arg Gln Gln Gln Ser Gly Arg Gly Trp Tyr Leu Gly Leu Asn Lys Glu
                165                 170                 175
Gly Glu Ile Met Lys Gly Asn His Val Lys Lys Asn Lys Pro Ala Ala
                180                 185                 190
His Phe Leu Pro Lys Pro Leu Lys Val Ala Met Tyr Lys Glu Pro Ser
                195                 200                 205
Leu His Asp Leu Thr Glu Phe Ser Arg Ser Gly Ser Gly Thr Pro Thr
                210                 215                 220
Lys Ser Arg Ser Val Ser Gly Val Leu Asn Gly Gly Lys Ser Met Ser
225                 230                 235                 240
His Asn Glu Ser Thr
                245

<210> SEQ ID NO 10
<211> LENGTH: 247
<212> TYPE: PRT
<213> ORGANISM: Artificial Sequence
<220> FEATURE:
<223> OTHER INFORMATION: Synthetic amino acid sequence:hFHF-4A

<400> SEQUENCE: 10

Met Ala Ala Ala Ile Ala Ser Gly Leu Ile Arg Gln Lys Arg Gln Ala
  1               5                  10                  15
Arg Glu Gln His Trp Asp Arg Pro Ser Ala Ser Arg Arg Arg Ser Ser
                 20                  25                  30
Pro Ser Lys Asn Arg Gly Leu Cys Asn Gly Asn Leu Val Asp Ile Phe
                 35                  40                  45
Ser Lys Val Arg Ile Phe Gly Leu Lys Lys Arg Arg Leu Arg Arg Gln
 50                  55                  60
Asp Pro Gln Leu Lys Gly Ile Val Thr Arg Leu Tyr Cys Arg Gln Gly
 65                  70                  75                  80
Tyr Tyr Leu Gln Met His Pro Asp Gly Ala Leu Asp Gly Thr Lys Asp
                 85                  90                  95
Asp Ser Thr Asn Ser Thr Leu Phe Asn Leu Ile Pro Val Gly Leu Arg
                100                 105                 110
Val Val Ala Ile Gln Gly Val Lys Thr Gly Leu Tyr Ile Ala Met Asn
                115                 120                 125
Gly Glu Gly Tyr Leu Tyr Pro Ser Glu Leu Phe Thr Pro Glu Cys Lys
                130                 135                 140
Phe Lys Glu Ser Val Phe Glu Asn Tyr Tyr Val Ile Tyr Ser Ser Met
145                 150                 155                 160
```

```
Leu Tyr Arg Gln Gln Glu Ser Gly Arg Ala Trp Phe Leu Gly Leu Asn
                165                 170                 175

Lys Glu Gly Gln Ala Met Lys Gly Asn Arg Val Lys Lys Thr Lys Pro
            180                 185                 190

Ala Ala His Phe Leu Pro Lys Pro Leu Glu Val Ala Met Tyr Arg Glu
        195                 200                 205

Pro Ser Leu His Asp Val Gly Glu Thr Val Pro Lys Pro Gly Val Thr
210                 215                 220

Pro Ser Lys Ser Thr Ser Ala Ser Ala Ile Met Asn Gly Gly Lys Pro
225                 230                 235                 240

Val Asn Lys Ser Lys Thr Thr
            245

<210> SEQ ID NO 11
<211> LENGTH: 225
<212> TYPE: PRT
<213> ORGANISM: Artificial Sequence
<220> FEATURE:
<223> OTHER INFORMATION: Synthetic amino acid sequence: hFHF-3A

<400> SEQUENCE: 11

Met Ala Ala Leu Ala Ser Ser Leu Ile Arg Gln Lys Arg Glu Val Arg
1               5                   10                  15

Glu Pro Gly Gly Ser Arg Pro Val Ser Ala Gln Arg Arg Val Cys Pro
            20                  25                  30

Arg Gly Thr Lys Ser Leu Cys Gln Lys Gln Leu Leu Ile Leu Leu Ser
        35                  40                  45

Lys Val Arg Leu Cys Gly Gly Arg Pro Ala Arg Pro Asp Arg Gly Pro
50                  55                  60

Glu Pro Gln Leu Lys Gly Ile Val Thr Lys Leu Phe Cys Arg Gln Gly
65                  70                  75                  80

Phe Tyr Leu Gln Ala Asn Pro Asp Gly Ser Ile Gln Gly Thr Pro Glu
                85                  90                  95

Asp Thr Ser Ser Phe Thr His Phe Asn Leu Ile Pro Val Gly Leu Arg
            100                 105                 110

Val Val Thr Ile Gln Ser Ala Lys Leu Gly His Tyr Met Ala Met Asn
        115                 120                 125

Ala Glu Gly Leu Leu Tyr Ser Ser Pro His Phe Thr Ala Glu Cys Arg
130                 135                 140

Phe Lys Glu Cys Val Phe Glu Asn Tyr Tyr Val Leu Tyr Ala Ser Ala
145                 150                 155                 160

Leu Tyr Arg Gln Arg Arg Ser Gly Arg Ala Trp Tyr Leu Gly Leu Asp
                165                 170                 175

Lys Glu Gly Gln Val Met Lys Gly Asn Arg Val Lys Lys Thr Lys Ala
            180                 185                 190

Ala Ala His Phe Leu Pro Lys Leu Leu Glu Val Ala Met Tyr Gln Glu
        195                 200                 205

Pro Ser Leu His Ser Val Pro Glu Ala Ser Pro Ser Ser Pro Pro Ala
210                 215                 220

Pro
225

<210> SEQ ID NO 12
<211> LENGTH: 16
<212> TYPE: PRT
<213> ORGANISM: Artificial Sequence
<220> FEATURE:
```

```
<223> OTHER INFORMATION: Synthetic sequence

<400> SEQUENCE: 12

Arg Gln Ile Lys Ile Trp Phe Gln Asn Arg Arg Met Lys Trp Lys Lys
1               5                   10                  15
```

ISOLATED A-TYPE FHF N-TERMINAL DOMAIN PEPTIDES AND METHODS OF USE

CROSS-REFERENCE TO RELATED APPLICATIONS

This application is a U.S. National Phase Application of International Application No. PCT/US2010/033885 filed on May 6, 2010 and asserts priority to U.S. Provisional Patent Application No. 61/175,951 filed on May 6, 2009, all of which are hereby incorporated by reference in their entirety.

GOVERNMENT FUNDING

The invention described in this application was made with support from the National Institutes of Health, grant numbers R01-NS39906-07 and U54-NS41073-08. The U.S. government has certain rights in the invention.

BACKGROUND OF THE INVENTION

Ion channels are pore-forming proteins that help establish and control a small voltage gradient across the plasma membrane of living cells by allowing the flow of ions down their electrochemical gradient. One type of ion channel is a voltage-gated channel, which utilizes a change in the voltage across the membrane to open the ion channel.

In nerve and skeletal muscle cells, a stimulus that causes sufficient depolarization promptly causes voltage gated sodium channels (VGSCs) to open, allowing a small amount of Na+ to enter the cell down its electrochemical gradient. The influx of positive charge depolarizes the membrane further, thereby opening more Na+ channels, which admit more Na+ ions, causing still further depolarization.

In this way, VGSCs provide the sodium ion currents that allow excitable cells, such as cardiac muscle and nerve cells, to "fire" digital pulses called action potentials. At most moments in time, these channels are closed and nonconducting, and only open briefly when a cell's membrane is depolarized. Within milliseconds, VGSCs then undergo fast inactivation—a separate non-conducting state from which channels recover within milliseconds after membrane repolarization. VGSCs contain a so-called fast inactivation "particle" (or "gate") that binds to the open channel pore to induce inactivation. The cycle of Closed—fast→Open—fast→Inactivated—fast→Recovered states of VGSCs enables them to fuel firing of action potentials at high frequencies in some cells.

There have been attempts to induce inactivation of VGSCs. However, these methods often destroy the entire VGSC. Other methods block various types of ion channels without being channel specific.

Accordingly, there remains a need for a peptide capable of inducing long-term use-dependent inactivation selectively in VGSCs. Such a peptide has a therapeutic value for cardiac and neurological disorders characterized by high frequency firing rates.

SUMMARY OF INVENTION

In one aspect of the invention, an isolated A-type FHF N-terminal domain (ANTD) peptide is provided. The peptide includes an amino acid sequence at least 90% identical to one of SEQ ID NOS: 1-4. The ANTD peptide induces inactivation of voltage-gated sodium channels in a cell of a mammal.

In another aspect of the invention, an isolated nucleic acid molecule is provided. The nucleic acid molecule encodes an ANTD peptide that includes an amino acid sequence at least 90% identical to one of SEQ ID NOS: 1-4. The peptide induces inactivation of voltage-gated sodium channels in a cell of a mammal.

In another aspect of the invention, a vector is provided. The vector includes the nucleic acid molecule that encodes an ANTD peptide having an amino acid sequence at least 90% identical to one of SEQ ID NOS: 1-4.

In another aspect of the invention, a host cell is provided. The host cell includes the vector having a nucleic acid molecule that encodes an ANTD peptide having an amino acid sequence at least 90% identical to one of SEQ ID NOS: 1-4.

In another aspect of the invention, a method is provided for inducing long-term inactivation of voltage-gated sodium channels in a cell of a mammal in need thereof. The method includes administering to the mammal an isolated ANTD peptide having an amino acid sequence at least 90% identical to one of SEQ ID NOS: 1-4. The peptide induces long-term inactivation of voltage-gated sodium channels in the cell of the mammal. Mammals in need thereof include, for example, mammals suffering from cardiac arrhythmia, mammals in chronic pain, or mammals, i.e., humans, in need of cosmetic therapy.

BRIEF DESCRIPTION OF THE FIGURES

FIGS. 1A-1C collectively show an alignment of FHF protein sequences (A and B types).

FIG. 2 contains graphs showing FHF2A protein induces long-term inactivation of Nav1.6.

FIG. 6 contains graphs showing N-terminal FHF2A (ANTD) peptide induces long term inactivation of inward current and reduced excitability in cultured cerebellar granule neurons.

FIG. 7 contains graphs showing FHF2A protein induces long-term inactivation of Nav1.6 in a single cycle of membrane depolarization.

DETAILED DESCRIPTION OF THE INVENTION

ANTD Peptides

Figure 3:
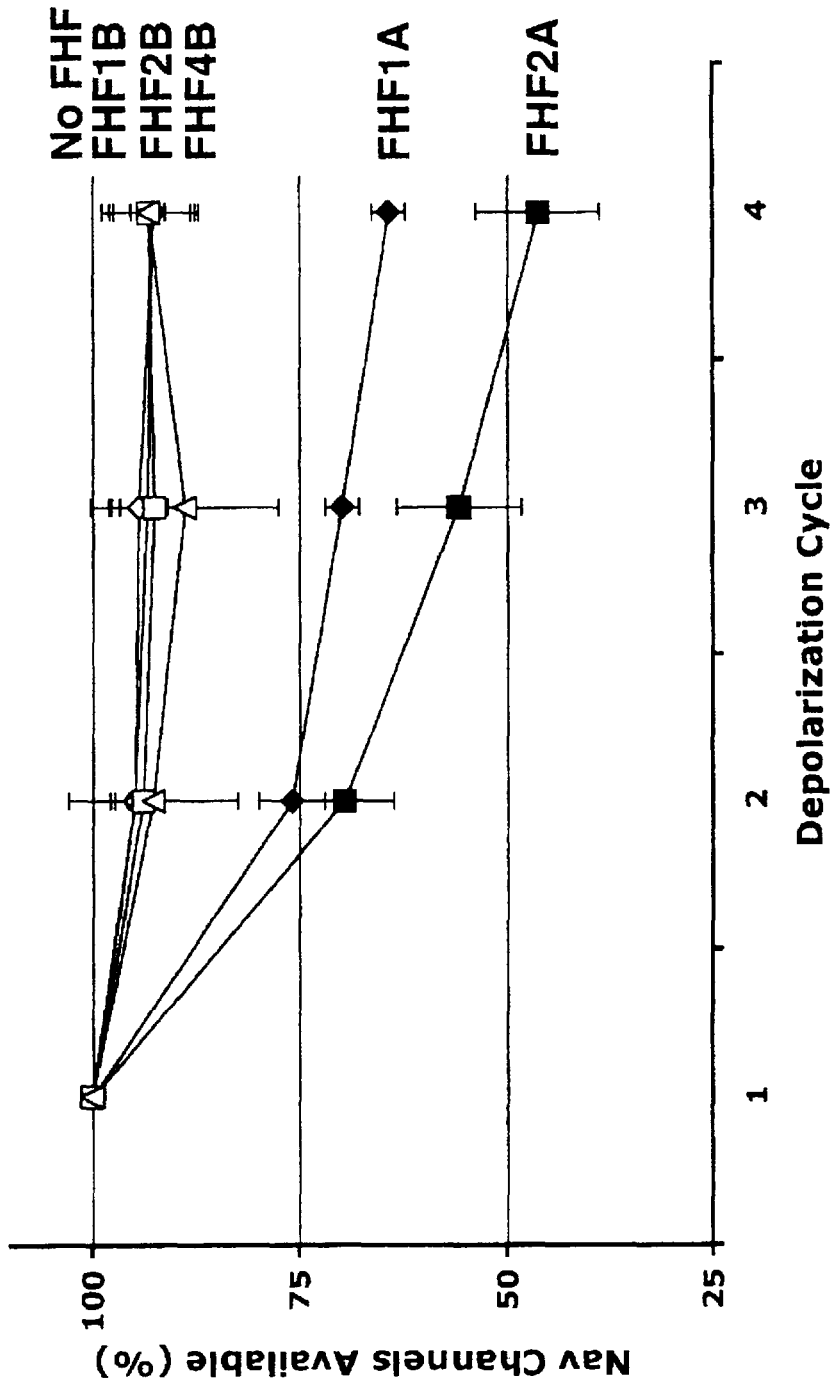
FIG. 3 contains graphs showing that only A-type FHFs induce long-term inactivation of Nav1.6.

In a first aspect of the invention, an isolated peptide is provided for inducing long-term use dependent inactivation (hereinafter "long-term inactivation") in voltage-gated sodium channels (VGSCs).

Fibroblast growth factor homologous factors (FHFs) constitute a family of proteins that bind to VGSCs and modify the kinetics of channel inactivation and recovery. Different FHFs exert distinct effects on channel dynamics. Some FHFs delay the inherent fast inactivation gate of channels and accelerate channel recovery, thereby rendering cells more excitable (Goldfarb et al. Neuron 55:449; 2007).

FIGS. 1A-1C collectively show an alignment of FHF protein sequences. The alignment depicts the conserved N-terminal region of A-type FHFs, the divergence past the first 20 residues, and the core homology among all FHFs (A and B types).

There also exists a separate form of inactivation that can only be accomplished with an accessory protein. This is a so-called "long-term use-dependent" inactivation, characterized by a fraction, e.g. 20-40%, of channels entering into a prolonged inactivation state from which they require far longer (0.1-1 sec) to recover (Rush et al. Eur. J. Neurosci. 23, 2551; 2006).

Applicants have discovered that a full length A-type FHF, such as FHF2A, has two separate functional regions, both of which are required for induction of long-term inactivation. One region is the FHF core homology domain (CHD), which contains a surface mediating direct FHF tethering to the cytoplasmic "tail" of VGSCs. The other region is the A-type FHF N-terminal domain (newly termed ANTD) that can insert itself into the open pore of a VGSC to induce long-term inactivation.

The VGSC intrinsic fast inactivation particle and the ANTD of the full length FHF compete in a mutually exclusive manner for binding to the open channel pore. The rate of ANTD binding to the pore is 3-5 times slower than the channel's intrinsic fast particle. Therefore, only 15-35% of channels are naturally long-term blocked by the ANTD portion of the full length FHF protein through each cycle of channel opening.

Applicants have demonstrated, using a mutant VGSC in which the fast inactivation particle was disabled, the A-type FHFs could drive nearly all channels into long-term inactivation in a single cycle of membrane depolarization and channel opening (See Example 6 and FIG. 7), thereby demonstrating that intrinsic fast inactivation limits FHF-induced long-term inactivation.

Accordingly, peptides according to the present invention include synthetic ANTD peptides that can induce long term inactivation in the VGSC without the VGSC being modified by the fast inactivation particle. The invention includes an ANTD peptide for each of the four A-type FHFs. The amino acid sequence of the ANTD for each of the A-type FHFs is set forth in Table 1.

TABLE 1

| Type 1A: | AAAIASSLIRQKRQARESNS | (SEQ ID NO. 1) |
|---|---|---|
| Type 2A: | AAAIASSLIRQKRQAREREK | (SEQ ID NO. 2) |
| Type 3A: | AALASSLIRQKREVREPGGS | (SEQ ID NO. 3) |
| Type 4A: | AAAIASGLIRQKRQAREQHW | (SEQ ID NO. 4) |

In a preferred embodiment, the ANTD is the peptide identified in SEQ ID NO. 2, corresponding to residues 2-21 of FHF2A.

When the ANTD peptide is injected into cells containing VGSCs in the absence of FHFs, the channels immediately become susceptible to long term inactivation. Unlike full length A-type FHF proteins, the isolated ANTD peptides of the invention do not modulate fast inactivation and do not alter the process of channel opening (activation).

Accordingly, the "long-term inactivation" of the VGSCs induced by the peptides of the invention is defined herein as the long-term use-dependent inactivation of VGSCs without modulation of intrinsic fast inactivation and without alteration of channel pore activation.

The rate of recovery from long-term inactivation induced by the ANTD peptide in mutant VGSCs bearing a disabled intrinsic inactivation particle is comparable to that induced by the complete FHF2A protein. By contrast, the rate of entry into long-term inactivation depends upon the peptide concentration; e.g., at 1 millimolar, the ANTD peptide induces faster onset of long-term inactivation than the native protein, resulting in a larger fraction of channels in long-term block per depolarization cycle. Sec FIG. 5. The ANTD peptide can also induce long-term inactivation of nearly all mutant VGSCs bearing a disabled intrinsic inactivation particle. These findings show that the ANTD peptides of the invention act as an independent long-term inactivation particle. Since channel tethering is not required for peptide action, the peptide is able to act on channels already occupied by native FHFs.

The ANTD peptides of the present invention may be synthesized by any of the methods well known in the art. Suitable methods for chemically synthesizing the protein include, for example, those described by Stuart and Young in "Solid Phase Peptide Synthesis." Second Edition, Pierce Chemical Company (1984), and in "Solid Phase Peptide Synthesis," Methods Enzymol. 289, Academic Press, Inc, New York (1997).

The ANTD peptides of the invention may include amino acid residues in addition to the residues of the sequences identified in Table 1. The additional amino acids should not interfere with their activity of inducing long term inactivation. In a preferred embodiment, the ANTD peptide is no longer than 60 amino acids, preferably no longer than 50 amino acids, more preferably no longer than 40 amino acid, and more preferably no longer than 30 amino acids, covalently joined by peptide bonds. Most preferably, the ANTD peptide consists essentially of the 20 amino acid residues identified in Table 1.

The ANTD peptides of the invention are isolated. As used herein, a peptide is said to be "isolated" or when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

The amino acids of the ANTD peptides of the present invention can be any amino acid. As used herein, the term "amino acid" is used to refer to any organic molecule that contains at least one amino group and at least one carboxyl group. Preferably, at least one amino group is at the α-position relative to the carboxyl group.

The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (lieu), leucine (Leu), lysine (Lys), methionine (Met), phenylalanine (Phe), proline (Pro), serine (Ser), threonine (Thr), tryptophan, (Trp), tyrosine (Tyr), and valine (Val).

The ANTD peptides of the invention can contain one or more non-naturally occurring amino acids. Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art.

Known modifications include, but are not limited to, acetylation, acylation. ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins-Structure and Molecular Properties, 2nd Ed., T. E. Creighton, W.H. Freeman and Company, New York (1993).

Many detailed reviews are available on this subject, such as by Wold, F., *Posttranslational Covalent Modification of Proteins*, B. C. Johnson, Ed., Academic Press, New York 1-12 (1983); Seifter et al. (Meth. Enzymol. 182: 626-646 (1990)) and Rattan et al. (Ann. IV: Y. Acad. Sci 663: 48-62 (1992)).

Accordingly, the ANTD peptides of the present invention also encompass derivatives or analogs in which a substituted amino acid residue is not one encoded by the genetic code, in which a substituent group is included, in which the mature ANTD peptide is fused with another compound, such as a compound to increase the half-life of the ANTD peptide (for example, polyethylene glycol), or in which the additional amino acids are fused to the mature ANTD peptide, such as a leader or secretory sequence or a sequence for purification of the mature ANTD peptide or a pro-protein sequence.

In a preferred embodiment, the ANTD peptide of the invention includes an acetyl group at the N-terminus of the peptide. In another preferred embodiment, the ANTD peptide includes an amide group at the C-terminus of the peptide.

The ANTD peptides of the invention are defined herein to include functional variants of the peptides identified in Table 1. In a preferred embodiment, the ANTD peptide of the invention includes those peptides that have 85%, preferably 90%, more preferably 95% amino acid sequence identity with the peptides identified in Table 1.

Percent amino acid sequence identity with respect to the ANTD peptide identified herein is defined as the percentage of amino acid residues in a candidate sequence that are identical with the amino acid residues in the specific ANTD peptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

For purposes herein, however, percent (%) amino acid sequence identity values are generated using the sequence comparison computer program NCBI-BLAST2 (Altschul et al., Nucleic Acids Res. 25:3389-3402 (1997)). The NCBI-BLAST2 sequence comparison program may be downloaded from the National Center for Biotechnology Information's website or otherwise obtained from the National Institutes of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Non-naturally occurring variants of the ANTD peptides of the present invention can readily be generated using recombinant techniques. Such variants include, but are not limited to deletions, additions and substitutions in the amino acid sequence of the ANTD peptide. For example, one class of substitutions is conserved amino acid substitutions. Such substitutions are those that substitute a given amino acid in an ANTD peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247: 1306-1310 (1990).

Amino acids that are essential for function can be identified by methods known in the art, such as site-directed mutagenesis or alanine-scanning mutagenesis (Cunningham et al., Science 244: 1081-1085 (1989). The latter procedure introduces single alanine mutations at every residue in the molecule. The resulting mutant molecules are then tested for biological activity, such as long term VGSC inactivation. Sites that are critical for binding partner/substrate binding can also be determined by structural analysis such as crystallization, nuclear magnetic resonance or photoaffinity labeling (Smith et al., R Mol. Biol. 224: 899-904 (1992); de Vos et al. Science 255: 306-312 (1992)).

The ANTD peptides of the present invention can be attached to heterologous sequences to form chimeric or fusion proteins. Such chimeric and fusion proteins comprise an ANTD peptide operatively linked to a heterologous protein having an amino acid sequence not substantially homologous to the ANTD peptide. "Operatively linked" indicates that the ANTD peptide and the heterologous protein are fused in-frame. The heterologous protein can be fused to the N-terminus or C-terminus of the ANTD peptide. Preferably, the fusion protein does not affect the activity of the ANTD peptide per se.

For example, the fusion protein can include, but is not limited to, enzymatic fusion proteins, for example beta-galactosidase fusions, yeast two-hybrid GAL fusions, poly-His fusions. MYC-tagged, HI-tagged and Ig fusions. Such fusion proteins, particularly poly-His fusions, can facilitate the purification of recombinant ANTD peptide. In certain host cells (e.g., mammalian host cells), expression and/or secretion of a protein can be increased by using a heterologous signal sequence.

In a preferred embodiment, the fusion protein includes a cell penetrating peptide fused to an ANTD peptide. Cell penetrating peptides are any peptides that increase the ability of the ANTD peptide to enter a cell. Such cell penetrating peptides are known in the art. See, e.g., Richard, et al., "Cell Penetrating Peptides," *J. Bio. Chem.*, 278(1):585-590 (2003); and Ulo Langel, Cell Penetrating Peptides. CRC Press (2002). In a preferred embodiment, the cell penetrating peptide is the sequence RQIKIWFQNRRMKWKK (SEQ ID NO: 12) from the *Antennapedia* protein.

A chimeric or fusion protein can be produced by standard recombinant DNA techniques. For example. DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). An ANTD peptide-encoding nucleic acid can be cloned into such an expression vector such that the fusion moiety is linked in-frame to the ANTD peptide.

Nucleic Acid Molecules

The present invention further provides isolated nucleic acid molecules that encode the ANTD peptides of the invention. Such nucleic acid molecules will consist of, consist essentially of, or comprise a nucleotide sequence that encodes one of the ANTD peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived.

However, there can be some flanking nucleotide sequences, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. For example, recombinant DNA molecules contained in a vector are considered isolated.

Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of any nucleic acid molecule that encodes the ANTD peptides provided in Table 1. A nucleic acid molecule consists of a nucleotide sequence when the nucleotide sequence is the complete nucleotide sequence of the nucleic acid molecule.

The present invention further provides nucleic acid molecules that consist essentially of the nucleic acid molecule that encodes an ANTD peptide provided in Table 1. A nucleic acid molecule consists essentially of a nucleotide sequence when such a nucleotide sequence is present with only a few additional nucleic acid residues in the final nucleic acid molecule.

The present invention further provides nucleic acid molecules that comprise a nucleic acid molecule that encodes an ANTD peptide provided in Table 1. A nucleic acid molecule comprises a nucleotide sequence when the nucleotide sequence is at least part of the final nucleotide sequence of the nucleic acid molecule. Thus, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides.

The nucleic acid molecules may contain genomic intronic sequences, 5' and 3' non-coding sequences, gene regulatory regions and non-coding intergenic sequences. In general such sequence features can readily be identified using computational tools known in the art. As discussed below, some of the non-coding regions, particularly gene regulatory elements such as promoters, are useful for a variety of purposes, e.g. control of heterologous gene expression, or a target for identifying gene activity modulating compounds.

As mentioned above, the isolated nucleic acid molecules include, but are not limited to, the sequence encoding the ANTD peptide alone; the sequence encoding the peptide and additional coding sequences, such as a leader or secretory sequence (e.g., a pre-pro or pro-protein sequence); and the sequence encoding the peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode obvious variants of the ANTD peptides of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptides described in Table 1 and to isolate cDNA and genomic clones that correspond to variants (alleles, orthologs, etc.) producing the same or related peptides shown in Table 1.

Vectors

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage A, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancer. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region, a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y. (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccina viruses, adenoviruses, lentiviruses, poxviruses, pseudorabies viruses, and retroviruses. Vectors may also be derived from combinations of these sources such as those derived from plasmid and bacteriophage genetic elements, e.g., cosmids and phagemids. Appropriate cloning and expression vectors for prokaryotic and eukaryotic hosts are described in Sambrook et. al., *Molecular Cloning: A Laboratory Manual,* 2nd. ed., Cold Spring Harbor Laboratory Press, Cold Spring Harbor, N.Y., (1989). Preferably, the vector is a lentivirus or adenovirus.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted, into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila,* animal cells such as COS and CHO cells, and plant cells.

As described herein, it may be desirable to express the peptide as a fusion protein. Accordingly, the invention provides fusion vectors that allow for the production of the ANTD peptides.

Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterotransporter. Typical fusion expression vectors include pGEX (Smith et al., Gene 67: 31-40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., Gene 69: 301-315 (1988)) and pET 1 Id (Studier et al. Gene Expression Technology,—Methods in Enymology 185: 60-89 (1990)).

Recombinant protein expression can be maximized in host bacteria by providing a genetic background wherein the host cell has an impaired capacity to proteolytically cleave the recombinant protein. (Gottesman. S., Gene Expression Technology. Methods in Ensymology 185, Academic Press, San Diego, Calif. (1990) 119-128). Alternatively, the sequence of the nucleic acid molecule of interest can be altered to provide preferential codon usage for a specific host cell, for example, *E. coli*. (Wadaetal., NucleicAcidsRes. 20: 2111-2118 (1992)).

The nucleic acid molecules can also be expressed by expression vectors that are operative in yeast. Examples of vectors for expression in yeast e.g, *S. cerevisiae* include pYepSecI (Baldari, et al. EMBO J 6 229-234 (1987)), pMFa (Kurjan et al., Cell 30: 933-943 (1982)), pJRY88 (Schultz et al., Gene 54: 113-123 (1987)), and pYES2 (Invikogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell. Biol. 3: 2156-2165 (1983)) and the pVL series (Lucklowetal., Virology 170: 31-39 (1989)).

In certain embodiments of the invention, the nucleic acid molecules described herein are expressed in mammalian cells using mammalian expression vectors. Examples of mammalian expression vectors include pCDM8 (Seed, B. Nature 329: 840 (1987)) and pMT2PC (Kaufman et al., EMBO 6: 187-195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook et al., *Molecular Cloning: A Laboratory Manual*. 2nd. ed., Cold Spring Harbor Laboratory Press. Cold Spring Harbor, N.Y. (1989).

Host Cells

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd. ed., Cold Spring Harbor Laboratory, Cold Spring Harbor Laboratory Press, Cold Spring Harbor, N.Y., (1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector.

Markers include tetracycline or ampicillin-resistance genes for prokaryotic host cells and dihydrofolate reductase or neomycin resistance for eukaryotic host cells. However, any marker that provides selection for a phenotypic trait can be used.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, appropriate secretion signals are incorporated into the vector. The signal sequence can be endogenous to the peptides or heterologous to these peptides.

Where the peptide is not secreted into the medium, the peptide can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Methods

In one embodiment, the invention provides a method for inducing long term inactivation in a cell using the ANTD peptides described above. For the purposes of this specification, inducing long-term inactivation of VGSCs in a cell is a detectable increase in the number of VGSCs in the targeted cells undergoing long-term use-dependent inactivation per depolarization cycle.

The amount of long-term inactivation desired in the cells can vary, for example, 10% to 90%, based upon the clinical application. For example, if the peptides are administered for cosmetic reasons to relax the tonal muscles in the face, a smaller amount, e.g., 10% of long-term inactivation of the muscle cells may be desired. If the peptides are administered to ameliorate chronic pain, a higher amount of inactivation, e.g., 90% may be desired.

VGSCs are expressed in a variety of "excitable" cells, such as neurons, myocytes and certain types of glia. As stated above, VGSCs provide the sodium ion currents that allow excitable cells, such as cardiac muscle and nerve cells, to "fire" digital pulses called action potentials. Thus, the peptides of the invention can be utilized in reducing the action potentials of these excitable cells.

VGSCs are also expressed in the cells of tonic muscles. Tonic muscles are those muscles in a mammal that contribute to muscle tone. These muscles include, for example, muscles of the face, calves, trapezius, etc.

Figure 5:
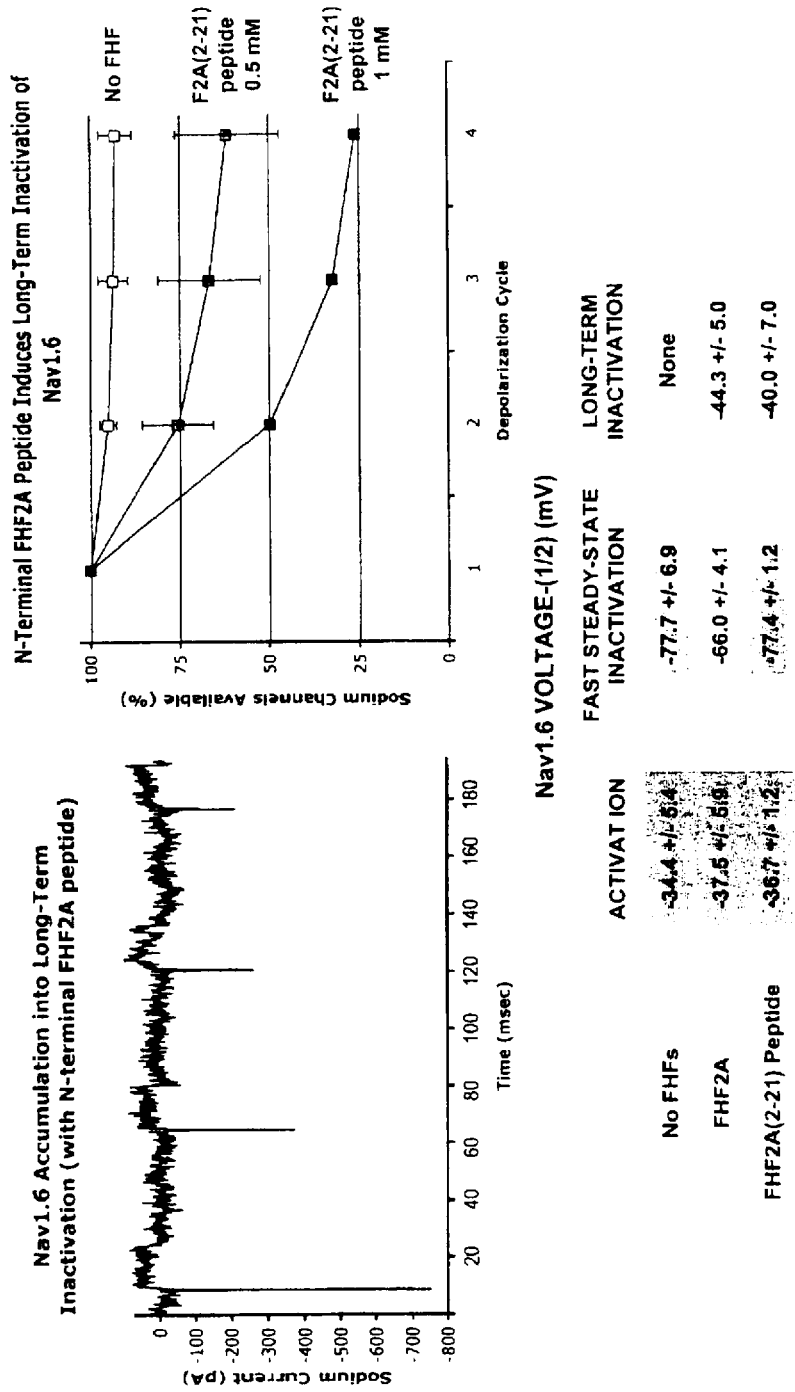
FIG. 5 contains graphs showing N-terminal FHF2A (ANTD) peptide induces Nav1.6 long-term inactivation.

In another embodiment, the invention provides a method for inducing long term inducing inactivation of VGSCs in a cell of a mammal in need thereof. The method includes administering the ANTD peptide of the invention to the mammal in an effective amount to induce the long term inactivation in the targeted cells, as desired. The effective amount is determined during the pre-clinical and clinical trials by methods well know to physicians and clinicians. FIG. 5 demonstrates that the peptide-induced effect on long-term inactivation is dose dependent.

The mammal treated in accordance with the invention can be any mammal, including, for example, farm animals, such as sheep, pigs, cows, and horses; pet animals, such as dogs and cats; laboratory animals, such as rats, mice and rabbits. In a preferred embodiment, the mammal is a human.

Mammals in need of long-term inactivation of VSGCs include, for example, mammals with heart arrhythmia. Presently, some arrhythmias are treated with anesthetics as a means of temporarily deactivating ion channels in myocytes involved in heart contraction.

Mammals in need of long term inactivation of VGSCs also include mammals with wrinkling of the skin. Presently, Botulinum toxin (Botox®) is used in cosmetic surgery as an anti-wrinkling agent based on its ability to relax facial muscles. The Botox® induces a paralysis of the facial muscles by blocking acetylcholine receptors. This muscle paralysis produces the unwanted side effect of a mask-like expression.

Instead of Botox®, the ANTD peptides of the invention can be administered to a mammal in need of an anti-wrinkling agent. The peptides induce long term inactivation in the cells of tonic muscles, where administered. The long term inactivation relaxes the tonic muscles, for example, facial muscles, thereby reducing wrinkling of the skin.

Mammals in need thereof can also include mammals suffering from chronic pain. Chronic pain is pain that persists longer than the temporal course of natural healing associated with a particular disease or injury. Pain is transmitted from sensory fibers to the brain. By administering an effective amount of ANTD peptide, the "firing" of the cells that make up these sensory fibers can be slowed, thereby reducing or eliminating the pain signals interpreted by the brain.

Sensory fibers differ from other types of fibers in the body by the spectrum of VGSCs. Thus, in a preferred embodiment, a specific isotype of ANTD peptide (see Table 1) is administered that is specific for the VGSCs in the sensory fibers desired to be inactivated.

Modes of Administration

Any method known to those in the art for contacting a cell, organ or tissue with a peptide may be employed. Suitable methods include in vitro, ex vivo, or in vivo methods.

In vitro methods typically include cultured samples. For example, a cell can be placed in a reservoir (e.g., tissue culture plate), and incubated with ANTD peptide under appropriate conditions suitable for inducing long term inactivation of VGSCs. Suitable incubation conditions can be readily determined by those skilled in the art.

Ex vivo methods typically include cells, organs or tissues removed from a mammal, such as a human. The cells, organs or tissues can, for example, be incubated with the peptide under appropriate conditions. The contacted cells, organs or tissues are normally returned to the donor, placed in a recipient, or stored for future use. Thus, the peptide is generally in a pharmaceutically acceptable carrier.

In vivo methods are typically limited to the administration of an ANTD peptide, such as those described above, to a mammal, preferably a human. The peptides useful in the methods of the present invention are administered to a mammal in an amount effective in inactivating VGSCs in a cell of the mammal or treating the mammal. The effective amount is determined during pre-clinical trials and clinical trials by methods familiar to physicians and clinicians.

An effective amount of a peptide useful in the methods of the present invention, preferably in a pharmaceutical composition, may be administered to a mammal in need thereof by any of a number of well-known methods for administering pharmaceutical compounds. The peptide may be administered systemically or locally.

In one embodiment, the peptide is administered intravenously. For example, the ANTD peptides useful in the methods of the present invention may be administered via rapid intravenous bolus injection. Preferably, however, the peptide is administered as a constant rate intravenous infusion.

The peptide may also be administered orally, topically, intranasally, intrathecally, intramuscularly, subcutaneously, or transdermally. In a preferred embodiment, transdermal administration of the ANTD peptides by methods of the present invention is by iontophoresis, in which the charged peptide is delivered across the skin by an electric current.

When administering the ANTD peptides for cosmetic therapy, for example, as part of an anti-wrinkling therapy, it is preferred the peptides be administered topically, subcutaneously, intramuscularly, or transdermally.

When administering the ANTD peptides for mammals with heart arrhythmia, it is preferred the peptides be administered intravenously.

When administering the ANTD peptides for mammals with chronic pain, it is preferred that peptides be administered orally, topically, intrathecally, intramuscularly, subcutaneously, or transdermally.

The peptides useful in the methods of the invention may also be administered to mammals by sustained release, as is known in the art. Sustained release administration is a method of drug delivery to achieve a certain level of the drug over a particular period of time. The level typically is measured by serum or plasma concentration.

A description of methods for delivering a compound by controlled release can be found in international PCT Application No. WO 02/083106. The PCT application is incorporated herein by reference in its entirety.

Any formulation known in the art of pharmacy is suitable for administration of the ANTD peptides useful in the methods of the present invention. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, topical, intranasal, intrathecal, subcutaneous, or transdermal administration, formulations of the ANTD peptides useful in the methods of the present inventions may utilize conventional diluents, carriers, or excipients etc., such as those known in the art to deliver the peptides. For example, the formulations may comprise one or more of the following: a stabilizer, a surfactant, preferably a nonionic surfactant, and optionally a salt and/or a buffering agent. The peptide may be delivered in the form of an aqueous solution, or in a lyophilized form.

The stabilizer may, for example, be an amino acid, such as for instance, glycine; or an oligosaccharide, such as for example, sucrose, tetralone, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the peptide.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the peptides useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

EXAMPLES

Example 1

Neuro2A cells expressing a tetrodotoxin (TTX)-resistant variant of sodium channel Nav1.6 were assayed in whole cell voltage clamp for Nav1.6 currents in the presence of TTX and inhibitors of potassium and calcium currents. The results are shown in FIG. 2. Nav1.6 currents were analyzed in cells without FHFs (upper panels) or after transient transfection with a DNA vector expressing full-length FHF2A protein (lower panels). The holding voltage was −90 mV. Cells were subjected to two 6 millisecond depolarizations at 0 mV separated by −90 mV interpulse recovery periods of 0.5 to 20 msec (left panels). All 40 command sweeps are shown.

While virtually all channels recover from inactivation within 20 milliseconds in the absence of FHF (upper left panel), approximately one-third of the channels do not rapidly recover in the presence of FHF2A (lower left panel). Alternatively, cells were subjected to four 16 millisecond depolarization cycles at 0 mV separated by 40 millisecond recoveries at −90 mV (right panels). In the absence of FHF, virtually all Nav1.6 channels recover between pulses, giving nearly the same inward current upon each subsequent depolarization (upper right panel). By contrast, in the presence of FHF2A protein, channels accumulate into a long-term inactivated state with each depolarization cycle (lower left panel).

Example 2

Neuro2A cells expressing TTX-resistant Nav1.6 were transfected with DNA expression vectors for FHF1A, FHF1B, FHF2A, FHF2B, or FHF4B. Transfected cells in the presence of TTX were subjected to four 16 millisecond depolarization cycles (0 mV) separated by 40 millisecond recovery periods (−90 mV), and peak inward Nav1.6-mediated sodium currents were recorded for each depolarization.

The results are shown in FIG. 3. Only the A-type FHFs (FHF1A, FHF2A) induce long-term inactivation, while FHF1B, FHF2B, and FHF4B do not.

Example 3

A Neuro2A cell expressing TTX-resistant Nav1.6 and transfected to express FHF2A was analyzed for the voltage dependence of steady state inactivation, long-term inactivation, and activation, using specific voltage command protocols. For steady state inactivation, cells were held at different "test command" voltages for 60 milliseconds followed immediately by further depolarization to 0 mV; the residual peak current derives from channels not inactivated (i.e. still available). For long term inactivation, cells were held at different "test command" voltages for 60 milliseconds, with each test command followed by 40 millisecond recovery at −90 mV before depolarization to 0 mV; peak current derives from channels that have not undergone long-term inactivation. For activation, cells were depolarized to different "test command" voltages, and peak inward currents were converted to percent maximum conductance to reflect percentage of channels transiently activated.

Figure 4:
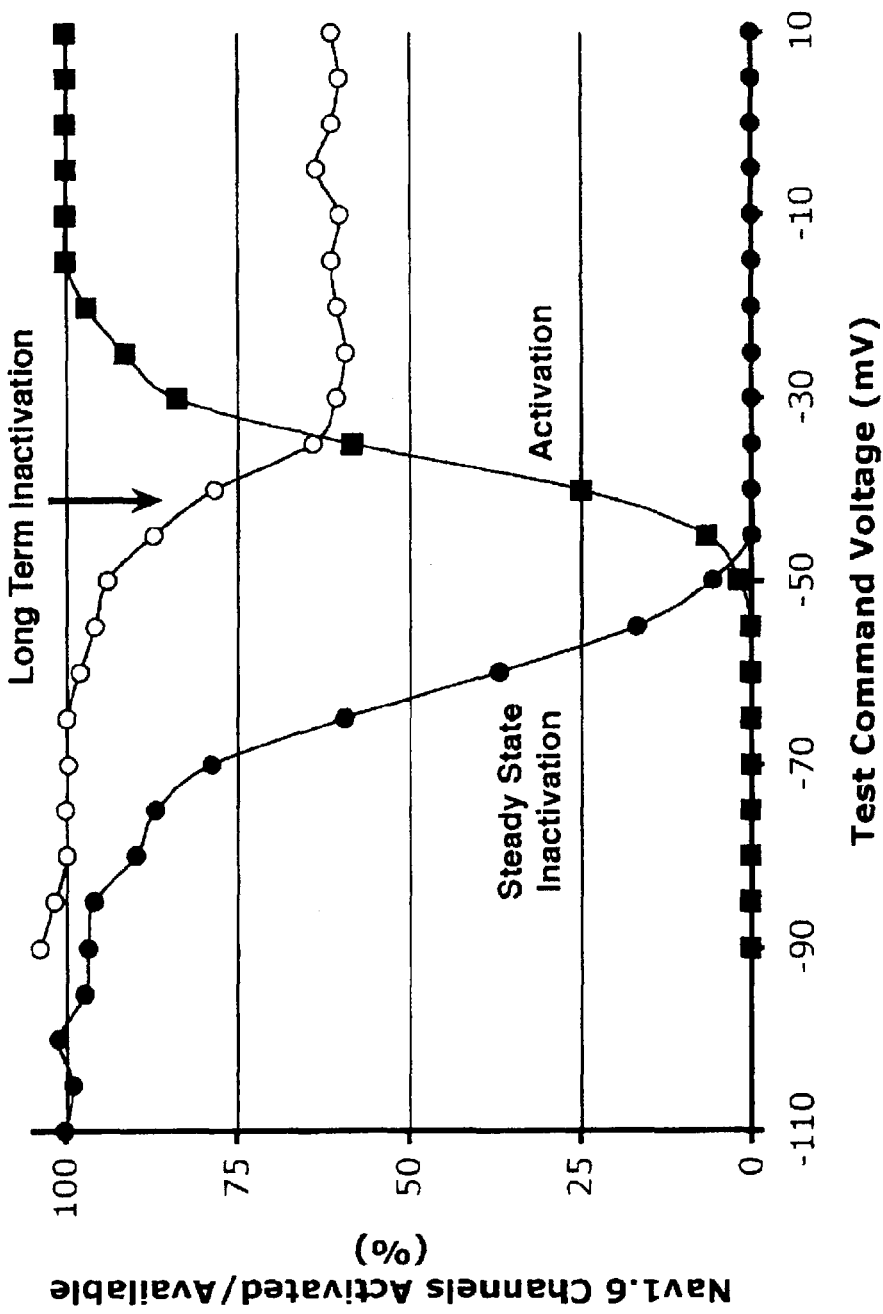
FIG. 4 is a graph showing Nav1.6 long-term inactivation and steady state inactivation are distinct inactivation states with different voltage dependences.

The results are shown in FIG. 4. The data shows that long-term inactivation occurs at a far more depolarized voltage than steady state inactivation, suggesting a different mechanism of inactivation requiring greater voltage-dependent channel transitions. Furthermore, only 35-40% of channels undergo long-term inactivation; this percentage is not increased by further depolarization, but is increase by further depolarization cycles (FIGS. 2, 3).

Example 4

Neuro2A cells expressing TTX-resistant Nav1.6 were analyzed for TTX-resistant sodium currents following whole cell patch clamp using pipette solution containing peptide corresponding to N-terminal residues 2-21 of FHF2A (referred to as ANTD, for A-type N-terminal domain). Peptide injected cells were subjected to four 16 millisecond depolarization cycles (0 mV) separated by 40 millisecond recovery periods (−90 mV), and peak inward Nav1.6-mediated sodium currents were recorded for each depolarization.

The results are shown in FIG. 5. Nav1.6 in a cell injected with 1 mM ANTD peptide shows robust accumulation into long-term inactivation (upper left panel). The use of ANTD at 0.5 mM also induced long-term inactivation, albeit to lesser degree (upper right panel), indicating that the peptide-induced effect is dose dependent. While full length FHF2A protein induces both long-term inactivation and a depolarizing shift in voltage dependence of steady state fast inactivation of Nav1.6, the ANTD peptide has no significant effect on steady state inactivation (lower table).

Example 5

Mouse cerebellar granule neurons were cultured for 14 days under conditions that promoted their maturation to a fully excitable state. These neurons were Whole cell patched and subjected to voltage clamp and current clamp protocols. In voltage clamp, neurons were depolarized four times for 16 milliseconds to 0 mV with 40 millisecond interpulse recoveries at −90 mV (left panels). In current clamp, positive current injection for 800 milliseconds was used to trigger firing of action potentials. A range of currents were tested, and only the recordings from currents giving highest frequency and amplitude of action potentials are shown (right panels).

The results are shown in FIG. 6. In the absence of FHF2A peptide injection, the neuron shows transient inward current (largely sodium current) and sustained outward current (potassium current) that are reproducible through four depolarization cycles (upper left panel). This same neuron in current clamp yields repetitive firing typical of granule neurons (upper right panel). In a neuron injected with N-terminal FHF2A (ANTD) peptide (1 mM), inward sodium currents decrease with each cycle of depolarization, while outward potassium currents are unaffected (lower left panel). This ANTD-treated neuron could generate only a single action potential upon current injection (lower right panel).

Example 6

Neuro2A cells expressing a tetrodotoxin (TTX)-resistant variant of sodium channel Nav1.6 were assayed in whole cell voltage clamp for Nav1.6 currents in the presence of TTX and inhibitors of potassium and calcium currents. Nav1.6 currents were analyzed in cells without FHFs (left panels—FIG. 7) or after transient transfection with a DNA vector expressing full-length FHF2A protein (right panels—FIG. 7).

The results, shown in FIG. 7, demonstrate that only the cells with the FHF2A protein are driven into long-term inactivation. Most impressively, the panel on the lower right of FIG. 7 shows nearly all channels being driven into long-term inactivation in a single cycle of membrane depolarization.

INCORPORATION OF SEQUENCE LISTING

Incorporated herein by reference in its entirety is the Sequence Listing for the application. The Sequence Listing is disclosed on a computer-readable ASCII text file titled, "sequence_listing.txt", created on Dec. 23, 2013. The sequence_listing.txt file is 16 kb in size.

What is claimed is:

1. An isolated A-type FHF N-terminal domain (ANTD) peptide consisting of SEQ ID NO: 2, wherein said peptide induces long-term inactivation of voltage-gated sodium channels in a mammalian cell.

2. The ANTD peptide according to claim 1, wherein the N-terminus of SEQ ID NO: 2 is acetylated.

3. The ANTD peptide according to claim 1, wherein the C-terminus of SEQ ID NO: 2 is amidated.

4. A composition comprising an ANTD peptide consisting of SEQ ID NO: 2 and a cell penetrating peptide, wherein said ANTD peptide induces long-term inactivation of voltage-gated sodium channels in a mammalian cell.

5. The composition according to claim 4, wherein said cell penetrating peptide is attached at the C-terminus of said ANTD peptide.

6. The composition according to claim 5, wherein said cell penetrating peptide is a portion of an *Antennapedia* protein.

7. The composition according to claim 6, wherein said cell penetrating peptide consists essentially of SEQ ID NO. 12.

8. A vector comprising a nucleic acid molecule that encodes an ANTD peptide, said peptide consisting of SEQ ID NO: 2, wherein said peptide induces long-term inactivation of voltage-gated sodium channels in a mammalian cell.

9. The vector according to claim 8, wherein said vector is a lentivirus.

10. The vector according to claim 8, wherein said vector is an adenovirus.

11. A host cell comprising a vector, said vector comprising a nucleic acid molecule that encodes an ANTD peptide consisting of SEQ ID NO: 2, wherein said peptide induces long-term inactivation of voltage-gated sodium channels in a mammalian cell.

12. A method for inducing inactivation of voltage-gated sodium channels in a mammalian cell, said method comprising contacting said cell with an isolated ANTD peptide consisting of SEQ ID NO: 2, wherein said peptide induces long-term inactivation of voltage-gated sodium channels in a mammalian cell.

13. The method according to claim 12, wherein said method further comprises contacting said cell with a cell penetrating peptide.

* * * * *

UNITED STATES PATENT AND TRADEMARK OFFICE
CERTIFICATE OF CORRECTION

PATENT NO. : 8,748,568 B2  
APPLICATION NO. : 13/319016  
DATED : June 10, 2014  
INVENTOR(S) : Mitchell Goldfarb and Dover Katarzyna Page 1 of 1

It is certified that error appears in the above-identified patent and that said Letters Patent is hereby corrected as shown below:

IN THE SPECIFICATION:

Column 15, Line 8

Now reads: "tetralone"

Should read: "tetralose"

Signed and Sealed this
Twenty-third Day of September, 2014

Michelle K. Lee
*Deputy Director of the United States Patent and Trademark Office*